US008912510B2

(12) United States Patent
Nishiwaki (10) Patent No.: US 8,912,510 B2
(45) Date of Patent: Dec. 16, 2014

(54) FLUORESCENCE OBSERVATION APPARATUS

(71) Applicant: Olympus Corporation, Tokyo (JP)

(72) Inventor: Daisuke Nishiwaki, Tokyo (JP)

(73) Assignee: Olympus Corporation, Tokyo (JP)

( * ) Notice: Subject to any disclaimer, the term of this patent is extended or adjusted under 35 U.S.C. 154(b) by 71 days.

(21) Appl. No.: 13/744,750

(22) Filed: Jan. 18, 2013

(65) Prior Publication Data

US 2013/0193345 A1 Aug. 1, 2013

(30) Foreign Application Priority Data

Jan. 30, 2012 (JP) ................................ 2012-017341

(51) Int. Cl.
*F21V 9/16* (2006.01)
*G01N 21/64* (2006.01)

(52) U.S. Cl.
CPC ............ *G01N 21/64* (2013.01); *G01N 21/6458* (2013.01)
USPC ...................................................... 250/458.1

(58) Field of Classification Search
USPC ........................................ 250/458.1; 359/368
See application file for complete search history.

(56) References Cited

U.S. PATENT DOCUMENTS

| 6,377,346 | B1* | 4/2002 | Vaisala et al. ................. 356/417 |
|---|---|---|---|
| 7,009,171 | B2* | 3/2006 | Sasaki ............................ 250/234 |
| 7,180,661 | B2* | 2/2007 | Sasaki ............................ 359/385 |
| 7,697,975 | B2* | 4/2010 | Zeng .............................. 600/473 |
| 2003/0076587 | A1* | 4/2003 | Stelzer et al. ................. 359/388 |
| 2004/0061073 | A1* | 4/2004 | Kitagawa .................... 250/458.1 |
| 2005/0082494 | A1* | 4/2005 | Motomura ................. 250/458.1 |
| 2005/0270639 | A1* | 12/2005 | Miki ............................. 359/381 |
| 2006/0086887 | A1* | 4/2006 | Nakata et al. ............... 250/201.3 |
| 2006/0109546 | A1* | 5/2006 | Namba et al. ................. 359/385 |
| 2007/0070350 | A1* | 3/2007 | Sugiyama et al. ............ 356/432 |
| 2007/0263282 | A1* | 11/2007 | Takamizawa et al. ......... 359/384 |
| 2008/0290293 | A1* | 11/2008 | Motomura .................. 250/458.1 |
| 2009/0040754 | A1* | 2/2009 | Brukilacchio et al. ........ 362/228 |
| 2009/0066934 | A1* | 3/2009 | Gao et al. ........................ 356/73 |
| 2009/0173892 | A1* | 7/2009 | Courtney et al. ........... 250/484.4 |
| 2009/0284948 | A1* | 11/2009 | Yamao et al. ................... 362/84 |
| 2010/0079857 | A1* | 4/2010 | Sasaki et al. .................. 359/353 |
| 2010/0084563 | A1* | 4/2010 | Ohno ....................... 250/363.01 |
| 2010/0193704 | A1* | 8/2010 | Pratt et al. .................. 250/459.1 |
| 2011/0096393 | A1* | 4/2011 | Araki ............................. 359/390 |
| 2011/0116165 | A1 | 5/2011 | Suzuki |
| 2011/0116261 | A1* | 5/2011 | Brukilacchio et al. ........ 362/231 |
| 2012/0305801 | A1* | 12/2012 | Kim et al. .................. 250/458.1 |

FOREIGN PATENT DOCUMENTS

| JP | 2011-90248 A | 5/2011 |
|---|---|---|
| JP | 2011-107257 A | 6/2011 |

* cited by examiner

*Primary Examiner* — David Porta
*Assistant Examiner* — Taeho Jo
(74) *Attorney, Agent, or Firm* — Holtz, Holtz, Goodman & Chick PC (57) ABSTRACT

Fluorescence observation apparatus includes laser scanning fluorescence observation unit and wide field fluorescence observation unit. The former unit includes: lasers; scanning unit that scans sample by laser light; and detector that detects fluorescence from the sample excited by the laser light. The latter unit includes: light source to planar-illuminate the sample; excitation filters that are selectively arranged on light path from the light source, and that correspond to the lasers, respectively; and two-dimensional detector that detects fluorescence from the sample excited by light that has passed through excitation filter arranged on light path from the light source. Each of the excitation filters has optical property in which center wavelength of transmissive band is approximately the same as oscillation wavelength of corresponding laser and bandwidth of transmissive band is approximately the same as tolerance width of oscillation wavelength of corresponding laser.

10 Claims, 9 Drawing Sheets

FLUORESCENCE OBSERVATION APPARATUS

CROSS REFERENCE TO RELATED APPLICATIONS

This application is based upon and claims the benefit of priority from prior Japanese Patent Application No. 2012-017341, filed Jan. 30, 2012, the entire contents of which are incorporated herein by this reference.

BACKGROUND OF THE INVENTION

1. Field of the Invention

The present invention relates to a fluorescence observation apparatus, and in particular, relates to a fluorescence observation apparatus including a fluorescence observation unit that observes a sample by scanning the sample with a laser light and a fluorescence observation unit that observes a sample by planar-illuminating the sample with light from a light source such as a mercury lamp.

2. Description of the Related Art

Conventionally, a fluorescence observation apparatus performs fluorescence observation in which a sample is observed by planar-illuminating the sample and detecting fluorescence by a two-dimensional detector (hereinafter, this type of observation will be referred to as wide field fluorescence observation), and fluorescence observation in which a sample is observed by using a scanning unit and scanning the sample with a laser light (hereinafter, this type of observation will be referred to as laser scanning fluorescence observation).

Apparatuses capable of performing both wide field fluorescence observation and laser scanning fluorescence observation are disclosed, for example, in Japanese Laid-open Patent Publication No. 2011-107257 and Japanese Laid-open Patent Publication No. 2011-090248. The microscope system disclosed in Japanese Laid-open Patent Publication No. 2011-107257 and Japanese Laid-open Patent Publication No. 2011-090248 switches and performs wide field fluorescence observation and laser scanning fluorescence observation by inserting a microscope switching mirror into an optical path.

As disclosed in Japanese Laid-open Patent Publication No. 2011-107257 and Japanese Laid-open Patent Publication No. 2011-090248, even if both a unit for performing wide field fluorescence observation (hereinafter, this type of unit will be referred to as a wide field fluorescence observation unit) and a unit for performing laser scanning fluorescence observation (hereinafter, this type of unit will be referred to as a laser scanning fluorescence observation unit) are provided for the conventional fluorescence observation apparatuses, wide field fluorescence observation and laser scanning fluorescence observation are not performed at the same time. These observations are switched and either one is performed.

SUMMARY OF THE INVENTION

An aspect of the present invention provides a fluorescence observation apparatus comprising: a laser scanning fluorescence observation unit including two or more lasers, a scanning unit that scans a sample by laser light from the lasers, and a detector that detects fluorescence from the sample excited by the laser light; a wide field fluorescence observation unit including a light source to planar-illuminate the sample, two or more excitation filters that are selectively arranged on an optical path of light from the light source, and that correspond to the lasers, respectively, and a two-dimensional detector that detects a fluorescence from the sample, where the fluorescence is excited by light that has passed through an excitation filter arranged on an optical path of light from the light source; and a dichroic mirror that combines an optical path of the laser light with an optical path of light from the light source, wherein each of the excitation filters has an optical property in which a center wavelength of a transmissive band is approximately the same as an oscillation wavelength of a corresponding laser and a bandwidth of a transmissive band is approximately the same as a tolerance width of an oscillation wavelength of a corresponding laser.

BRIEF DESCRIPTION OF THE DRAWINGS

The present invention will be more apparent from the following detailed description when the accompanying drawings are referenced.

DESCRIPTION OF THE EMBODIMENTS

In the conventional fluorescence observation apparatuses that include both a wide field fluorescence observation unit and a laser scanning fluorescence observation unit, the two types of observation are not performed at the same time but are normally performed after they are switched. This is because the selection process of filters such as excitation filters or barrier filters tends to be complicated when both the wide field fluorescence observation and the laser scanning fluorescence observation are performed at the same time.

Before some embodiments of the present invention are explained, the reason why the selection process of filters tends to be complicated when both the wide field fluorescence observation and the laser scanning fluorescence observation are performed at the same time in the conventional fluorescence observation apparatuses will be explained in a specific manner.

It is general for a fluorescence observation apparatus to have a configuration in which barrier filters that block an excitation light are arranged in front of a detector in order to detect only fluorescence. In order to perform both of the two types of observations above at the same time, it is necessary to arrange, in front of a detector in a wide field fluorescence observation unit such as a charge coupled device (CCD), barrier filters that are not only capable of blocking an excitation light used in a wide field fluorescence observation unit but also capable of blocking an excitation light (laser light) used in a laser scanning fluorescence observation unit. In a similar manner, it is necessary to arrange, in front of a detector in a laser scanning fluorescence observation unit such as a photomultiplier tube (PMT), barrier filters that are not only capable of blocking an excitation light (laser light) used in a laser scanning fluorescence observation unit but also capable of blocking an excitation light used in a wide field fluorescence observation unit.

Moreover, it is general for a wide field fluorescence observation unit to have a configuration in which an excitation filter that selectively allows light of a wavelength necessary for excitation out of the light emitted from a light source to pass through is arranged on an exit optical path from a light source to a sample. In order to perform both of the two types of observations above at the same time, it is not sufficient to arrange an excitation filter that simply selects light of a wavelength necessary for excitation, but it is also necessary to arrange on an exit optical path an excitation filter capable of preventing the selected wavelength (excitation wavelength) from overlapping with a fluorescence wavelength to be detected by a laser scanning fluorescence observation unit.

As described above, in a fluorescence observation apparatus provided with a wide field fluorescence observation unit and a laser scanning fluorescence observation unit, filters such as barrier filters and excitation filters arranged in a unit on one side need to be selected not only in consideration of an excitation wavelength or fluorescence wavelength to be used in a unit on one side but also in consideration of an excitation wavelength or fluorescence wavelength to be used in a unit on the other side. For this reason, the selection of filters to be used, in particular, the selection of the combination of filters to be used, tends to be complicated.

Embodiment 1

Figure 1:
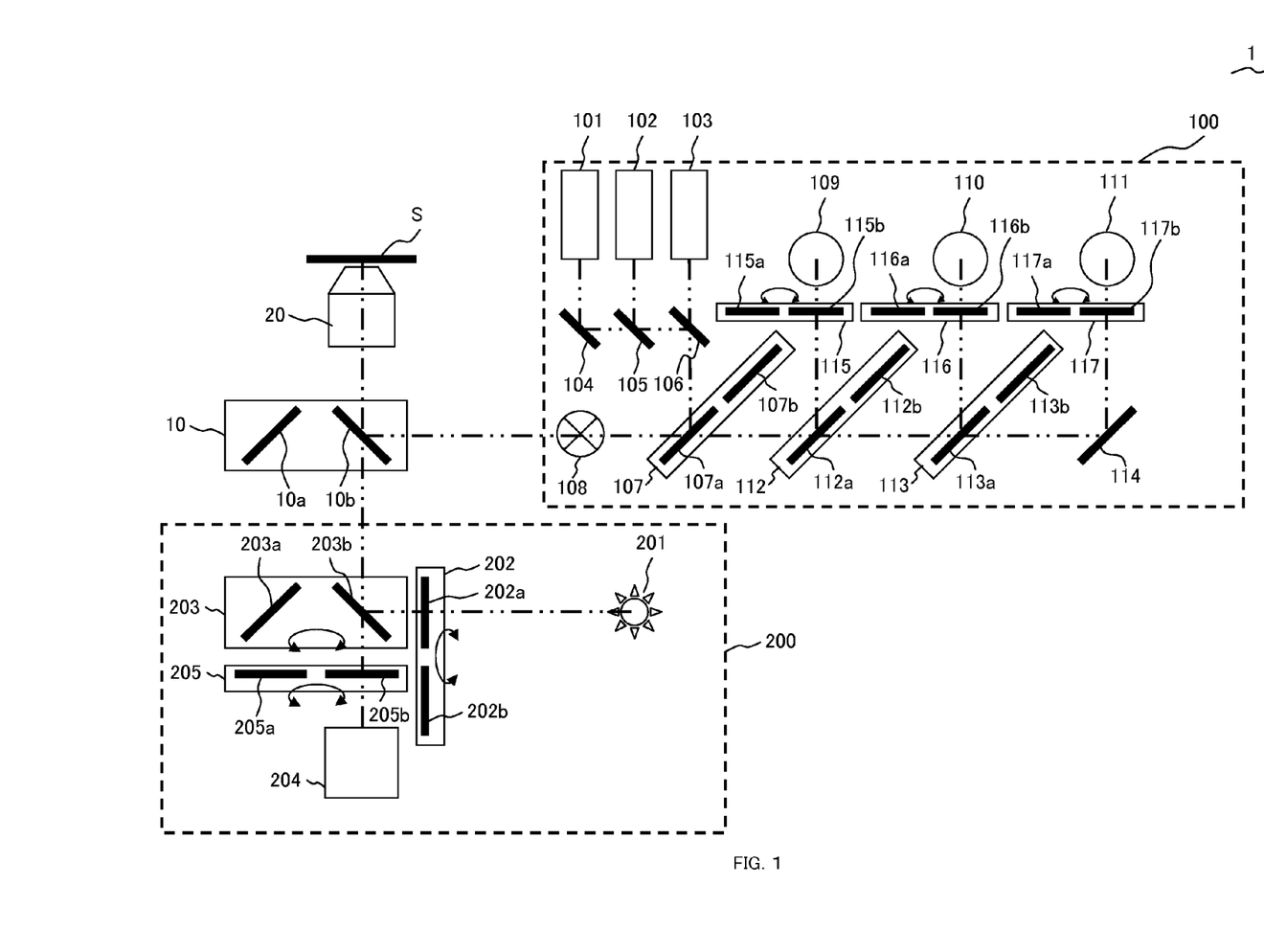
FIG. 1 illustrates an example of the configuration of a fluorescence observation apparatus according to Embodiment 1 of the present invention.

FIG. 1 illustrates an example of the configuration of a fluorescence observation apparatus according to the present embodiment. Firstly, the configuration of a fluorescence observation apparatus according to the present embodiment will be explained with reference to FIG. 1. In the actual apparatuses, a tube lens and a relay optical system that relays pupil, or the like is arranged as necessary at an earlier stage of a two-dimensional detector. In FIG. 1, however, a tube lens and a relay optical system or the like is omitted so as to illustrate a fluorescence observation apparatus in a schematic manner.

A fluorescence observation apparatus 1 illustrated in FIG. 1 as an example is provided with: a laser scanning fluorescence observation unit 100 that observes a sample S by using a scanning unit to scan the sample S with laser light; and a wide field fluorescence observation unit 200 that observes the sample S by planar-illuminating the sample S and by using a two-dimensional detector to detect fluorescence, where laser scanning fluorescence observation and wide field fluorescence observation may be performed at the same time.

The fluorescence observation apparatus 1 further includes: an objective lens 20; and a filter switching unit 10 that switches dichroic mirrors (i.e., a dichroic mirror 10a, and a dichroic mirror 10b) arranged on an optical axis of the objective lens 20.

The filter switching unit 10 switches the dichroic mirrors arranged on an optical axis according to the excitation wavelength and fluorescence wavelength used in the laser scanning fluorescence observation unit 100 and the wide field fluorescence observation unit 200. The filter switching unit 10 switches the dichroic mirrors such that a dichroic mirror with an optical property, where light at the excitation wavelength and fluorescence wavelength used by the laser scanning fluorescence observation unit 100 are reflected and light at the excitation wavelength and fluorescence wavelength used by the wide field fluorescence observation unit 200 is transmitted, will be arranged on an optical axis. Accordingly, the dichroic mirrors in the filter switching unit 10 function as a unit that combines an optical path of the laser light from the laser scanning fluorescence observation unit 100 with an optical path of the light from a light source of the wide field fluorescence observation unit 200.

The filter switching unit 10 may further include a half mirror, and when an excitation wavelength used by the laser scanning fluorescence observation unit 100 is the same as an excitation wavelength used by the wide field fluorescence observation unit 200, a half mirror may be arranged on an optical path in the filter switching unit 10.

The laser scanning fluorescence observation unit 100 includes: two or more lasers (i.e., a laser 101, a laser 102, and a laser 103); a galvanometer mirror 108 as a scanning unit that scans a sample by laser light from the two or more lasers; and two or more photomultipliers (i.e., a PMT 109, a PMT 110, and a PMT 111) as detectors that detect fluorescence from a sample S excited by laser light.

The laser scanning fluorescence observation unit 100 further includes two or more barrier filters selectively arranged by a filter switching unit 10 between the dichroic mirrors in the filter switching unit 10 and PMTs, where each of the barrier filters corresponds to each of the lasers. In particular, a filter switching unit 115 is included between the dichroic mirrors in the filter switching unit 10 and a PMT 109, and the filter switching unit 115 includes a barrier filter 115a that corresponds to a laser 101, a barrier filter 115b that corresponds to a laser 102, and a barrier filter (not illustrated) that corresponds to a laser 103. In a similar manner, a filter switching unit 116 placed between the dichroic mirrors in the filter switching unit 10 and a PMT 110, and a filter switching unit 117 placed between the dichroic mirrors in the filter switching unit 10 and a PMT 111 also include two or more barrier filters (i.e., a barrier filter 116a, a barrier filter 116b, a barrier filter 117a, a barrier filter 117b, or the like) that correspond to the lasers, respectively.

Here, the term "barrier filter that corresponds to a laser" refers to a barrier filter having an optical property that allows the fluorescence emitted from a fluorescent material whose excitation wavelength is an oscillation wavelength of a corresponding laser to pass through, and that sufficiently cuts off the light with a wavelength other than the wavelength of the fluorescence above, in particular, the light with an oscillation wavelength of the two or more lasers included in the fluorescence observation apparatus 1.

The laser scanning fluorescence observation unit 100 also includes: a unit that guides laser light from the two or more lasers onto the same optical path (e.g., a mirror 104, a dichroic mirror 105, and a dichroic mirror 106); a unit that combines the optical path of a laser light with the optical path of a fluorescence (e.g., a filter switching unit 107, adichroic mirror 107a, and a dichroic mirror 107b); and a unit that guides a fluorescence from each of fluorescent material to each of two or more PMTs (e.g., a filter switching unit 112, a dichroic mirror 112a, a dichroic mirror 112b, a filter switching unit 113, a dichroic mirror 113a, a dichroic mirror 113b, and a mirror 114).

The wide field fluorescence observation unit 200 includes: a mercury lamp 201 as a light source for planar-illuminating the sample S; two or more excitation filters that are selectively arranged on an optical path of the light from the mercury lamp 201 by a filter switching unit 202, and that correspond to the two or more lasers, respectively (e.g., an excitation filter 202a corresponding to the laser 101, an excitation filter 202b corresponding to the laser 102, and an excitation filter (not illustrated) corresponding to the laser 103); and a CCD 204 as a two-dimensional detector for detecting fluorescence from the sample S, where the sample S is excited by light that has passed through an excitation filter arranged on an optical path.

Here, the term "excitation filter that corresponds to a laser" refers to an excitation filter with an optical property in which the center wavelength of a transmissive band is approximately the same as an oscillation wavelength of a corresponding laser and the bandwidth of a transmissive band is approximately the same as the tolerance width of an oscillation wavelength of a corresponding laser.

In the wide field fluorescence observation unit 200, the excitation filter 202a has an optical property in which the center wavelength of a transmissive band is approximately the same as an oscillation wavelength of the corresponding laser 101 and the bandwidth of a transmissive band is approximately the same as the tolerance width of an oscillation wavelength of a corresponding laser 101. Moreover, the excitation filter 202b has an optical property in which the center wavelength of a transmissive band is approximately the same as an oscillation wavelength of the corresponding laser 102 and the bandwidth of a transmissive band is approximately the same as the tolerance width of an oscillation wavelength of a corresponding laser 102. Further, the excitation filter (not illustrated) corresponding to the laser 103 has an optical property in which the center wavelength of a transmissive band is approximately the same as an oscillation wavelength of the corresponding laser 103 and the bandwidth of a transmissive band is approximately the same as the tolerance width of an oscillation wavelength of the corresponding laser 103.

The wide field fluorescence observation unit 200 further includes two or more barrier filters selectively arranged by a filter switching unit 205 between the dichroic mirrors in the filter switching unit 10 and the CCD 204, where each of the barrier filters corresponds to each of the lasers. The filter switching unit 205 includes a barrier filter 205a that corresponds to the laser 101 and a barrier filter 205b that corresponds to the laser 102, and further includes a barrier filter that corresponds to a laser 103 (not illustrated).

The definition of a barrier filter that corresponds to a laser is as described above. Accordingly, a barrier filter included in the laser scanning fluorescence observation unit 100 and a barrier filter included in the wide field fluorescence observation unit 200 which correspond to the same laser may have the same optical property.

In addition to the above, the wide field fluorescence observation unit 200 includes a unit that combines an optical path of the light from the mercury lamp 201 with an optical path of fluorescence (i.e., a filter switching unit 203, a dichroic mirror 203a, and a dichroic mirror 203b).

Figure 2A:
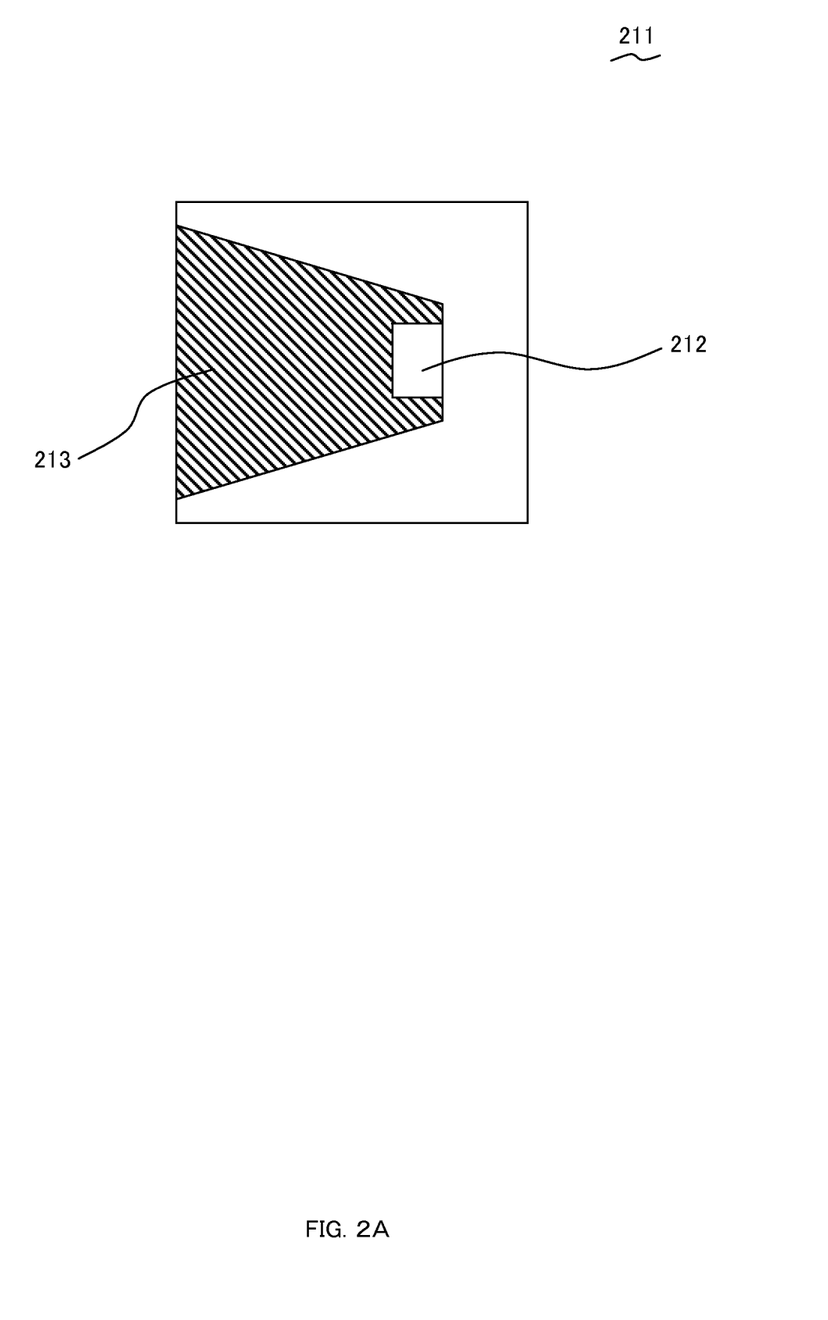
FIG. 2A illustrates an example of the modification of a light source of a wide field fluorescence observation unit included in a fluorescence observation apparatus according to Embodiment 1 of the present invention.
Figure 2B:
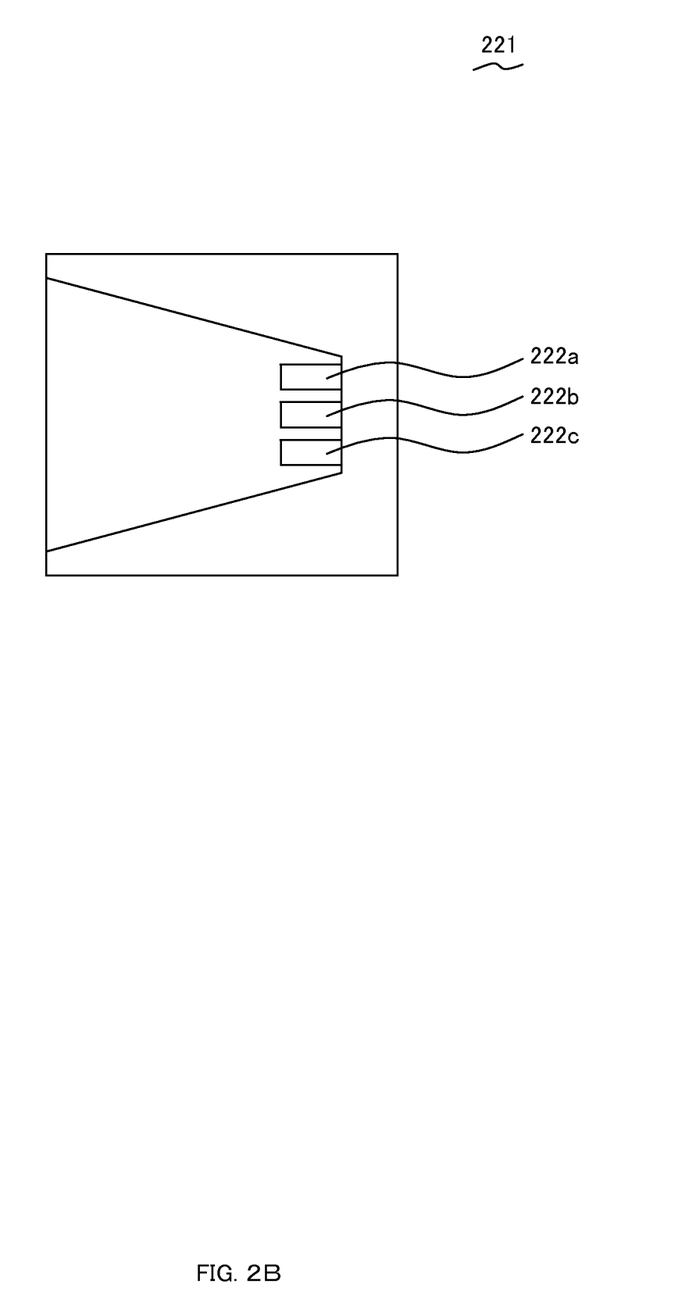
FIG. 2B illustrates another example of the modification of a light source of a wide field fluorescence observation unit included in a fluorescence observation apparatus according to Embodiment 1 of the present invention.

In FIG. 1, the mercury lamp 201 is illustrated as an example as a light source of the wide field fluorescence observation unit 200, but the light source of the wide field fluorescence observation unit 200 is not limited to the mercury lamp 201. It is desired that the light source of the wide field fluorescence observation unit 200 be a light source with a continuous or discrete light source wavelength including the oscillation wavelengths of two or more lasers. For this reason, the fluorescence observation apparatus 1 may include a white LED light source 211 provided with a sealing agent 213, including a fluorescent material around an LED chip 212, instead of the mercury lamp 201, as illustrated in FIG. 2A. Moreover, the fluorescence observation apparatus 1 may include a white LED light source 221 provided with two or more LED chips (e.g., an LED chip 222a, an LED chip 222b, and an LED chip 222c), instead of the mercury lamp 201, as illustrated in FIG. 2B.

Figure 3:
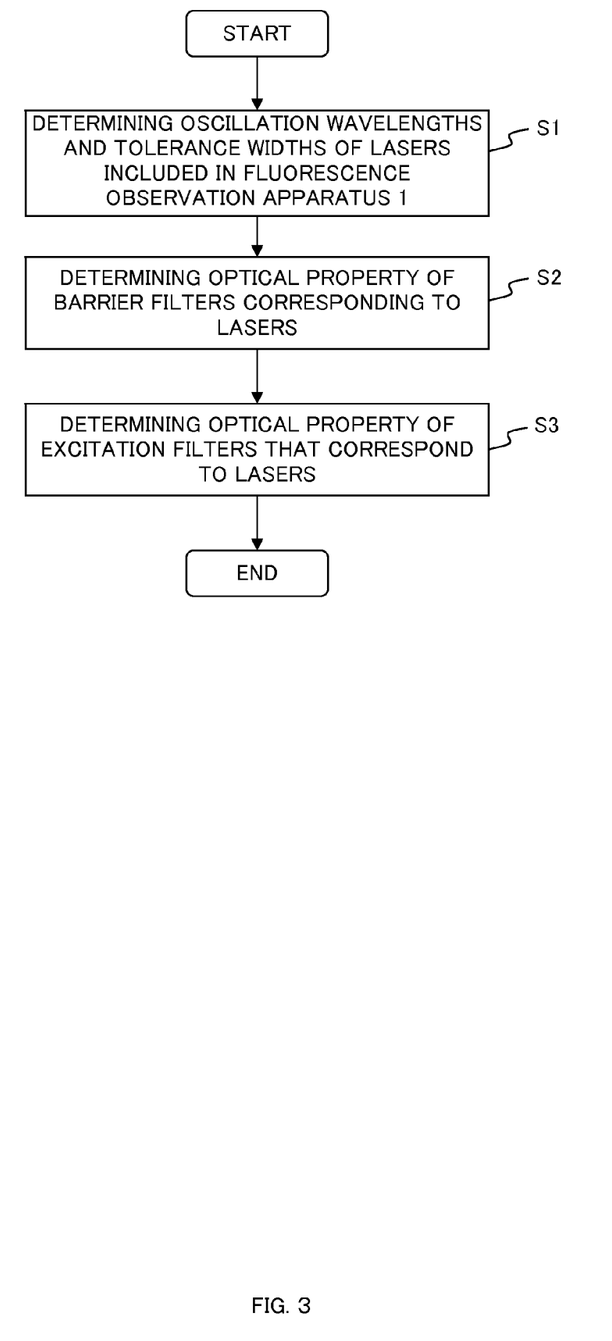
FIG. 3 is a flowchart depicting the procedure for determining the optical property of a barrier filter and an excitation filter included in a fluorescence observation apparatus according to Embodiment 1 of the present invention.
Figure 4A:
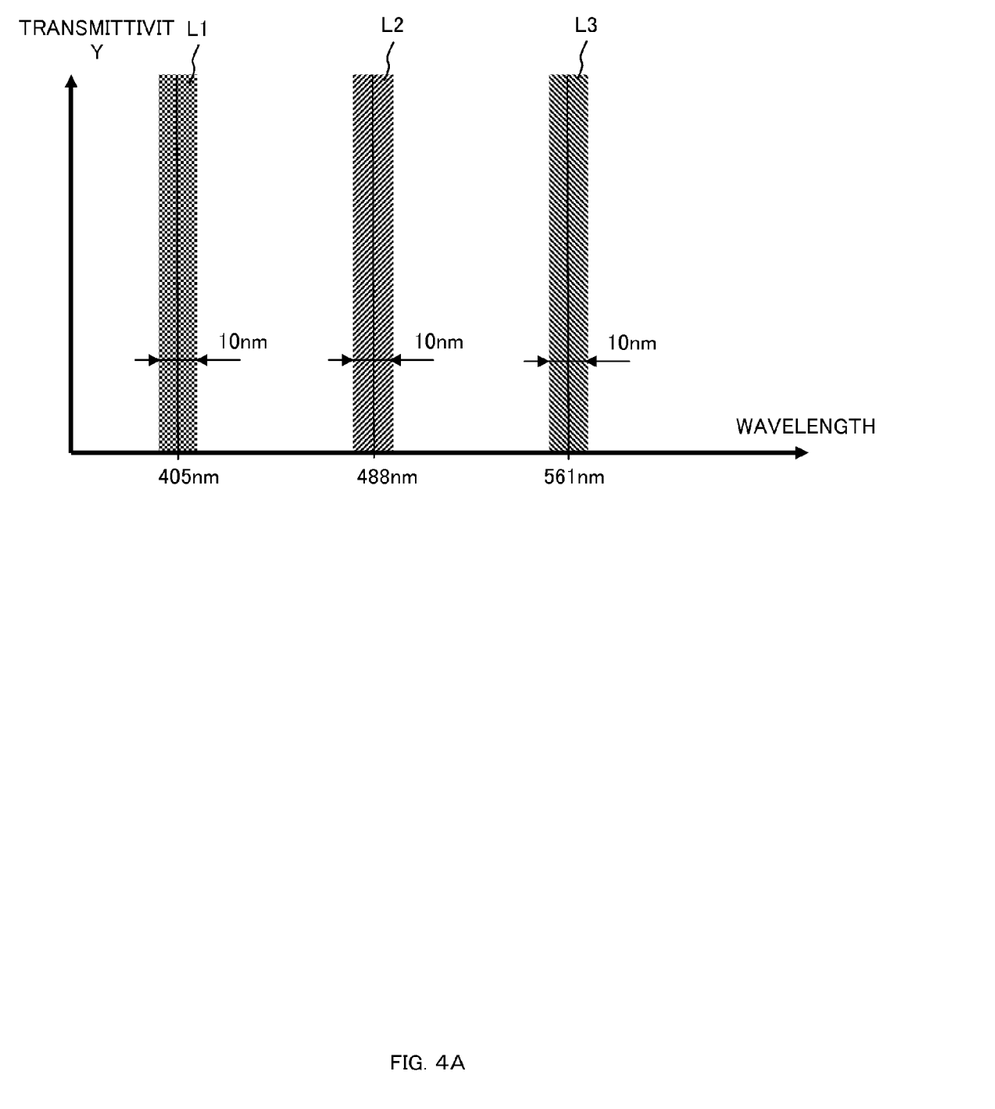
FIG. 4A illustrates the tolerance zone of the oscillation wavelengths of lasers included in a fluorescence observation apparatus according to Embodiment 1 of the present invention.
Figure 4B:
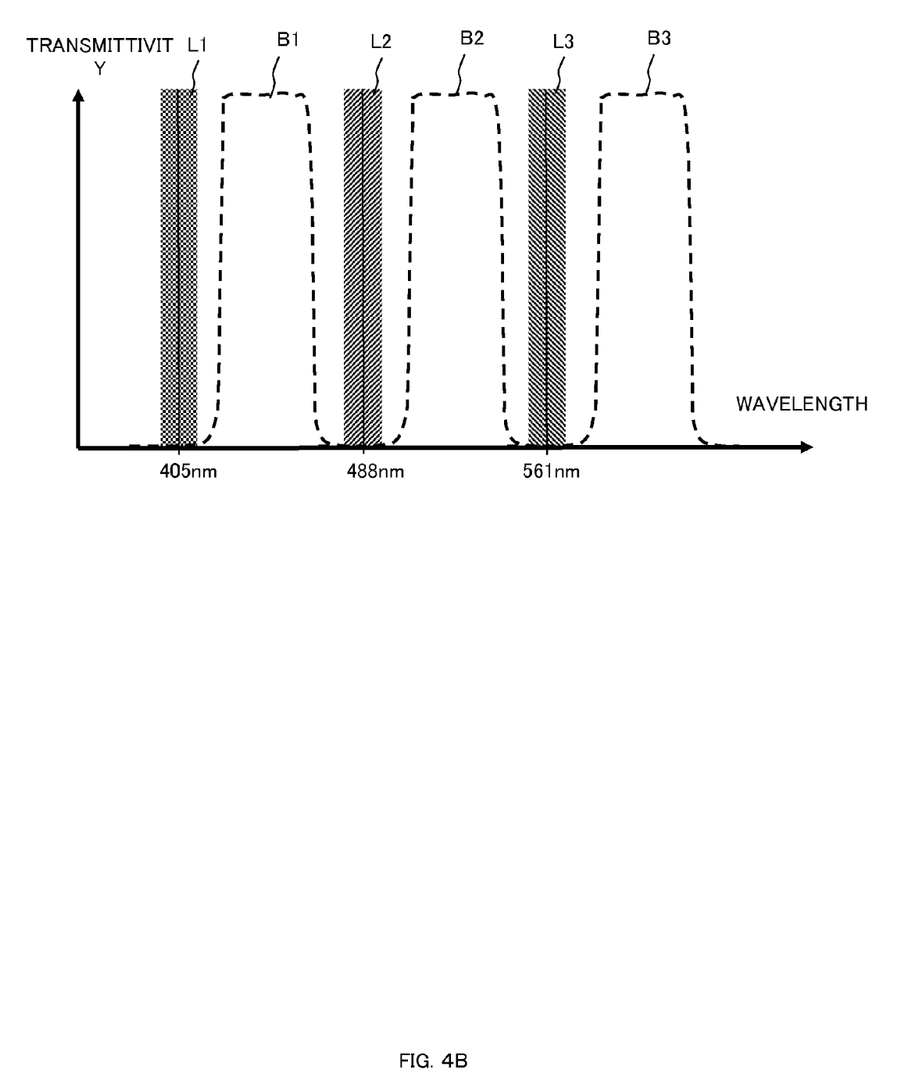
FIG. 4B illustrates the optical property of barrier filters included in a fluorescence observation apparatus according to Embodiment 1 of the present invention.
Figure 4C:
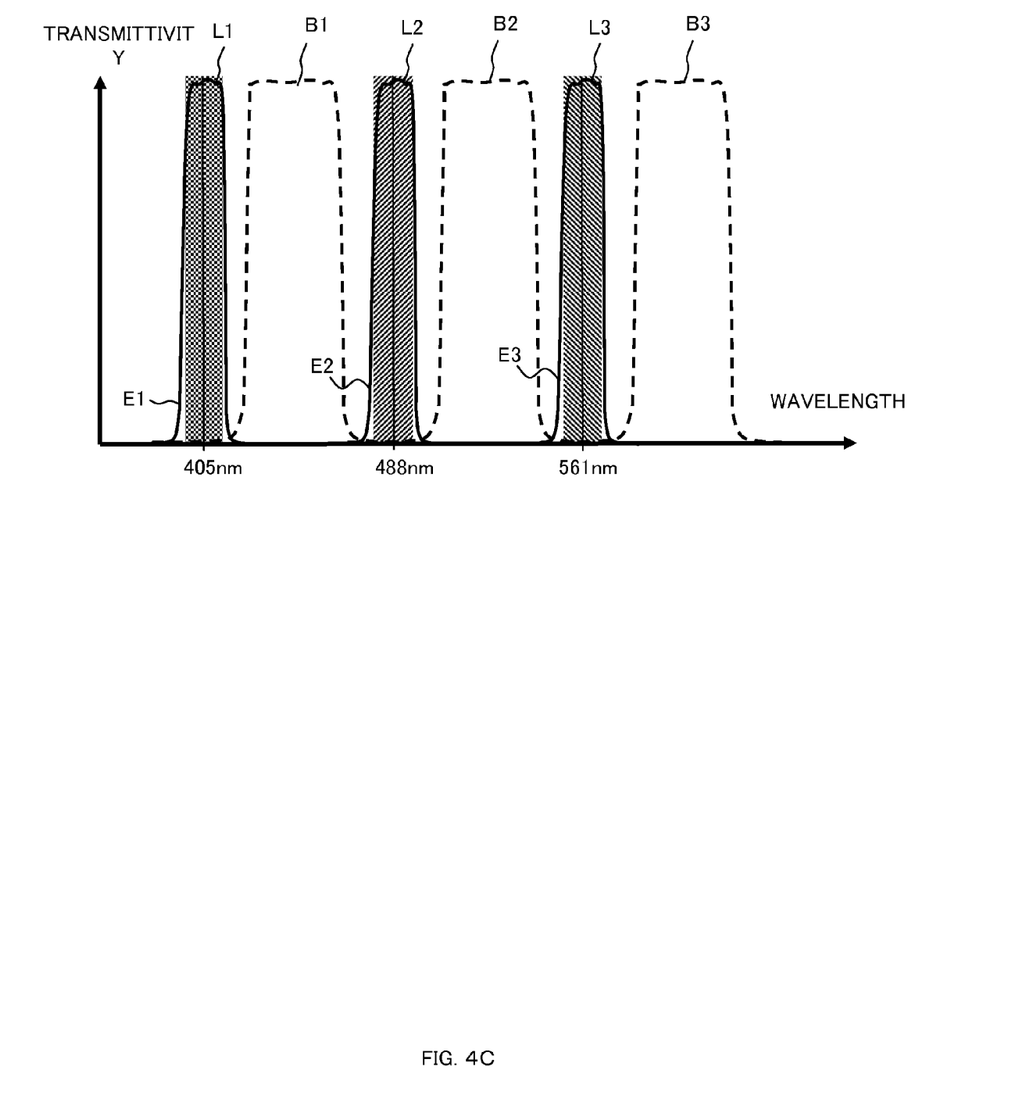
FIG. 4C illustrates the optical property of excitation filters included in a fluorescence observation apparatus according to Embodiment 1 of the present invention.

FIG. 3 is a flowchart depicting the procedure for determining the optical property of a barrier filter and an excitation filter included in the fluorescence observation apparatus according to the present embodiment. FIG. 4A illustrates the tolerance zone of the oscillation wavelengths of lasers included in a fluorescence observation apparatus according to the present embodiment. FIG. 4B illustrates the optical property of barrier filters included in a fluorescence observation apparatus according to the present embodiment. FIG. 4C illustrates the optical property of excitation filters included in a fluorescence observation apparatus according to the present embodiment. The procedure determining the optical property of a barrier filter and excitation filter to be included in the fluorescence observation apparatus 1 will be explained with reference to FIG. 3 and FIG. 4A through FIG. 4C.

Firstly, the oscillation wavelength and the tolerance width of two or more lasers are determined according to the specifications of the two or more lasers included in the fluorescence observation apparatus 1 (see step S1 in FIG. 3). In FIG. 4A, a tolerance zone L1 of the oscillation wavelengths of the laser 101 where the oscillation wavelength is 405 nm and the tolerance of the oscillation wavelength is ±5 nm, a tolerance zone L2 of the oscillation wavelengths of the laser 102 where the oscillation wavelength is 488 nm and the tolerance of the oscillation wavelength is ±5 nm, and a tolerance zone L3 of the oscillation wavelengths of the laser 103 where the oscillation wavelength is 561 nm and the tolerance of the oscillation wavelength is ±5 nm are illustrated.

Next, the optical property of the barrier filters corresponding to the lasers included in the fluorescence observation apparatus 1 is determined according to the oscillation wavelengths and the tolerance width of the two or more lasers determined in step S1 (see step S2 in FIG. 3). In FIG. 4B, the optical property of the barrier filter that corresponds to the laser 101, the optical property of the barrier filter that corresponds to the laser 102, and the optical property of the barrier filter that corresponds to the laser 103 are depicted as a line B1, a line B2, and a line B3, respectively.

In particular, the optical property of the barrier filter that corresponds to the laser 101 (see line B1) is determined such that a transmissive band will be formed between the tolerance zone L1 and the tolerance zone L2 and in a band (for example, between 420 nm and 470 nm) including the fluorescence wavelength of a fluorescent material that is excited by a laser light of the laser 101. In more detail, the determination is made such that the transmittivity of the barrier filter will be equal to or greater than a specified optical density (for example, OD6 or OD7) in the tolerance zone L1 and the tolerance zone L2.

In a similar manner, the optical property of the barrier filter that corresponds to the laser 102 (see line B2) is determined such that a transmissive band will be formed between the tolerance zone L2 and the tolerance zone L3 and in a band (for example, between 500 nm and 550 nm) including the fluorescence wavelength of a fluorescent material that is excited by a laser light of the laser 102. In more detail, the determination is made such that the transmittivity of the barrier filter will be equal to or greater than a specified optical density (for example, OD6 or OD7) in the tolerance zone L2 and the tolerance zone L3. Further, the optical property of the barrier filter that corresponds to the laser 103 (see line B3) is determined such that a transmissive band will be formed in a band (for example, between 580 nm and 620 nm) exceeding the tolerance zone L3 and in a band including the fluorescence wavelength of a fluorescent material that is excited by a laser light of the laser 103. In more detail, the determination is made such that the transmittivity of the barrier filter will be equal to or greater than a specified optical density (for example, OD6 or OD7) in the tolerance zone L3.

Finally, the optical property of the excitation filters that correspond to the respective lasers included in the fluorescence observation apparatus 1 is determined according to the oscillation wavelengths and the tolerance width of the two or more lasers determined in step S1 (see step S3 in FIG. 3). In this case, it is desired that the optical property of the barrier filters determined in step S2 also be taken into consideration. In FIG. 4C, the optical property of the excitation filter corresponding to the laser 101, the optical property of the excitation filter corresponding to the laser 102, and the optical property of the excitation filter corresponding to the laser 103 are depicted as a line E1, a line E2, and a line E3, respectively.

In particular, the optical property of the excitation filter (see line E1) that corresponds to the laser 101 is determined so as to have an optical property where the center wavelength of a transmissive band is approximately the same as an oscillation wavelength 405 nm of the corresponding laser 101 and the bandwidth of a transmissive band is approximately the same as a tolerance width 10 nm of an oscillation wavelength of the corresponding laser 101. More desirably, the multiplication product of the transmittivity of the barrier and excitation filters that correspond to the laser 101 is determined to be greater than a specified optical density (for example, OD6 or OD7).

In a similar manner, the optical property of the excitation filter (see line E2) that corresponds to the laser 102 is determined so as to have an optical property where the center wavelength of a transmissive band is approximately the same as an oscillation wavelength 488 nm of the corresponding laser 102 and the bandwidth of a transmissive band is approximately the same as a tolerance width 10 nm of an oscillation wavelength of the corresponding laser 102. More desirably, the multiplication product of the transmittivity of the barrier and excitation filters that correspond to the laser 102 is determined to be greater than a specified optical density (for example, OD6 or OD7). The optical property of the excitation filter (see line E3) that corresponds to the laser 103 is determined so as to have an optical property where the center wavelength of a transmissive band is approximately the same as an oscillation wavelength 561 nm of the corresponding laser 103 and the bandwidth of a transmissive band is approximately the same as a tolerance width 10 nm of an oscillation wavelength of the corresponding laser 103. More desirably, the multiplication product of the transmittivity of the barrier and excitation filters that correspond to the laser 103 is determined to be greater than a specified optical density (for example, OD6 or OD7).

As described above, in the fluorescence observation apparatus 1, the optical property of a barrier filter and excitation filter included in the fluorescence observation apparatus 1 may be determined according to the characteristics of the lasers included the laser scanning fluorescence observation unit 100 with no reference to the characteristics of a light source included the wide field fluorescence observation unit 200. Accordingly, the same number of types of filters as that of the lasers is sufficient, and the types of filters may be significantly reduced. This is achieved by deliberately limiting the options of an excitation wavelength to be used in a wide field fluorescence observation unit, which are chosen without much restraint, to the options of an excitation wavelength that may be used in a laser scanning fluorescence observation unit.

In FIG. 3, an example in which the optical property of the excitation filter is determined after the optical property of barrier filters are determined is depicted, but the optical property of barrier filters may be determined after the optical property of the excitation filter is determined.

Figure 5:
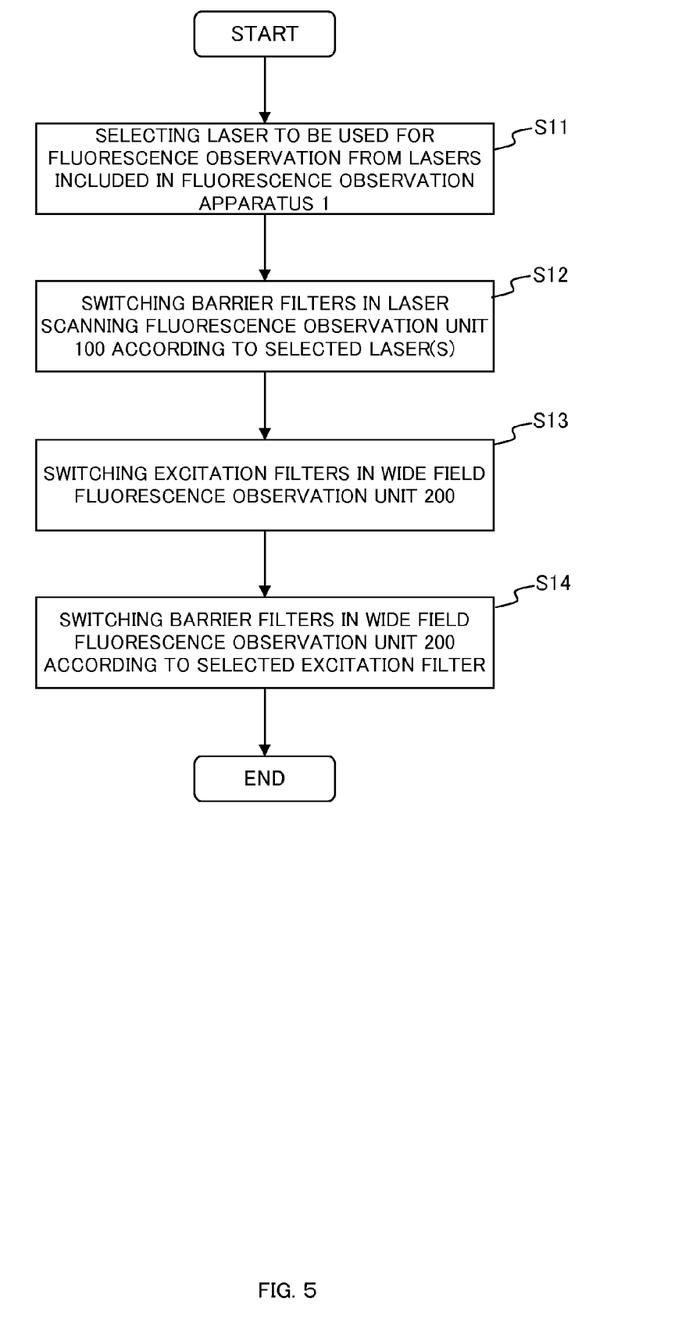
FIG. 5 is a flowchart illustrating the procedure for switching between barrier filters and for switching between excitation filters, which are included in a fluorescence observation apparatus according to the present embodiment, in the cases where both the wide field fluorescence observation and the laser scanning fluorescence observation are performed at the same time.

FIG. 5 is a flowchart illustrating the procedure for switching between barrier filters and for switching between excitation filters, which are included in a fluorescence observation apparatus according to the present embodiment, in the cases where both the wide field fluorescence observation and the laser scanning fluorescence observation are performed at the same time. The procedure for switching between barrier filters and for switching between excitation filters will be explained with reference to FIG. 5.

Firstly, a laser to be used for fluorescence observation is selected from two or more lasers included in the laser scanning fluorescence observation unit 100 (step S11), and the excitation wavelength and fluorescence wavelength to be used in the laser scanning fluorescence observation unit 100 are determined. Note that the number of lasers to be used for fluorescence observation is not limited to one. As two or more PMTs are provided in the fluorescence observation apparatus 1, two or more lasers, for example, the laser 101 and the laser 102, may be selected and used at the same time. Next, cases in which, for example, the laser 101 is selected as well as cases in which, for example, the laser 101 and the laser 102 are selected will be explained below.

Next, barrier filters in the laser scanning fluorescence observation unit 100 are switched according to the laser or lasers selected in step S11 (step S12). When the laser 101 is selected in step S11, the filter switching unit 115 is used to arrange the barrier filter 115a that corresponds to the laser 101 between the dichroic mirrors in the filter switching unit 10 and the PMT 109 used for fluorescence observation. When the laser 101 and the laser 102 are selected in step S11, further, the filter switching unit 116 is used to arrange the barrier filter 116b that corresponds to the laser 102 between the dichroic mirrors in the filter switching unit 10 and the PMT 110 used for fluorescence observation.

Next, an excitation filter in the wide field fluorescence observation unit 200 is selected and switched thereto (step S13). For example, when a sample is to be observed by exciting different fluorescent materials between the laser scanning fluorescence observation unit 100 and the wide field fluorescence observation unit 200 and the laser 101 is selected in step S11, the filter switching unit 202 is used to arrange an excitation filter that corresponds to another laser excluding the laser 101 on an optical path of the light from the mercury lamp 201. In particular, the excitation filter 202b corresponding to the laser 102, for example, is arranged. When the laser 101 and the laser 102 are selected in step S11, the filter switching unit 202 is used to arrange an excitation filter (not illustrated) that corresponds to the other laser 103 excluding the laser 101 and laser 102 on an optical path of the light from the mercury lamp 201.

When the sample is to be observed by exciting the same fluorescent material between the laser scanning fluorescence observation unit 100 and the wide field fluorescence observation unit 200, the filter switching unit 202 is used to arrange an excitation filter that corresponds to the laser selected in step S11 on an optical path of the light from the mercury lamp 201. In particular, when the laser 101 is selected in step S11, the excitation filter 202a corresponding to the laser 101 is arranged. When the laser 101 and the laser 102 are selected in step S11, the excitation filter 202a corresponding to the laser 101 or the excitation filter 202b corresponding to the laser 102 is arranged.

Finally, barrier filters in the wide field fluorescence observation unit 200 are switched according to the excitation filter selected in step S12 (step S14). When the laser 101 is selected in step S11 and the excitation filter 202b corresponding to the laser 102 is arranged in step S13, the filter switching unit 205 is used to arrange a barrier filter 205b that corresponds to the laser 102 between the dichroic mirrors in the filter switching unit 10 and the CCD 204. When the laser 101 and the laser 102 are selected in step S11 and the excitation filter corresponding to the laser 103 is arranged in step S13, the filter switching unit 205 is used to arrange a barrier filter (not illustrated) that corresponds to the laser 103 between the dichroic mirrors in the filter switching unit 10 and the CCD 204.

As described above, in the cases where both the wide field fluorescence observation and the laser scanning fluorescence observation are performed at the same time in the fluorescence observation apparatus 1, a barrier filter that is arranged on an optical path in the laser scanning fluorescence observation unit 100 may be uniquely determined from a relatively small number of types of barrier filters as a user selects a laser to be used according to the fluorescent material to be used for observation. A user may select any excitation filter to be arranged on an optical path in the wide field fluorescence observation unit 200 according to the fluorescent material to be used for observation. A barrier filter that is arranged on an optical path in the wide field fluorescence observation unit 200 may be uniquely determined from a relatively small number of types of barrier filters as an excitation filter is selected. Accordingly, an appropriate combination of a barrier filter and an excitation filter may easily be selected.

According to the fluorescence observation apparatus 1 in the present embodiment, the optical property of an excitation filter corresponds to the optical property of one of the lasers, and thus it is possible to handle the light transmitted through an excitation filter from the mercury lamp 201 like a laser light. In other words, it is possible to regard the mercury lamp 201 in the wide field fluorescence observation unit 200 as two or more lasers in the laser scanning fluorescence observation unit 100. Accordingly, commonality in the optical property among barrier filters may be achieved in the laser scanning fluorescence observation unit 100 and the wide field fluorescence observation unit 200.

Moreover, it is possible to select various filters such as a barrier filter or an excitation filter in the laser scanning fluorescence observation unit 100 and the wide field fluorescence observation unit 200 according to the excitation wavelength and fluorescence wavelength to be used in the subject unit, without reference to the excitation wavelength and fluorescence wavelength used in the other unit. As a result, even in the cases where both the observation using the laser scanning fluorescence observation unit 100 (laser scanning fluorescence observation) and the observation using the wide field fluorescence observation unit 200 (wide field fluorescence observation) are performed at the same time, an appropriate combination of a barrier filter and an excitation filter may easily be selected.

Embodiment 2

Figure 6:
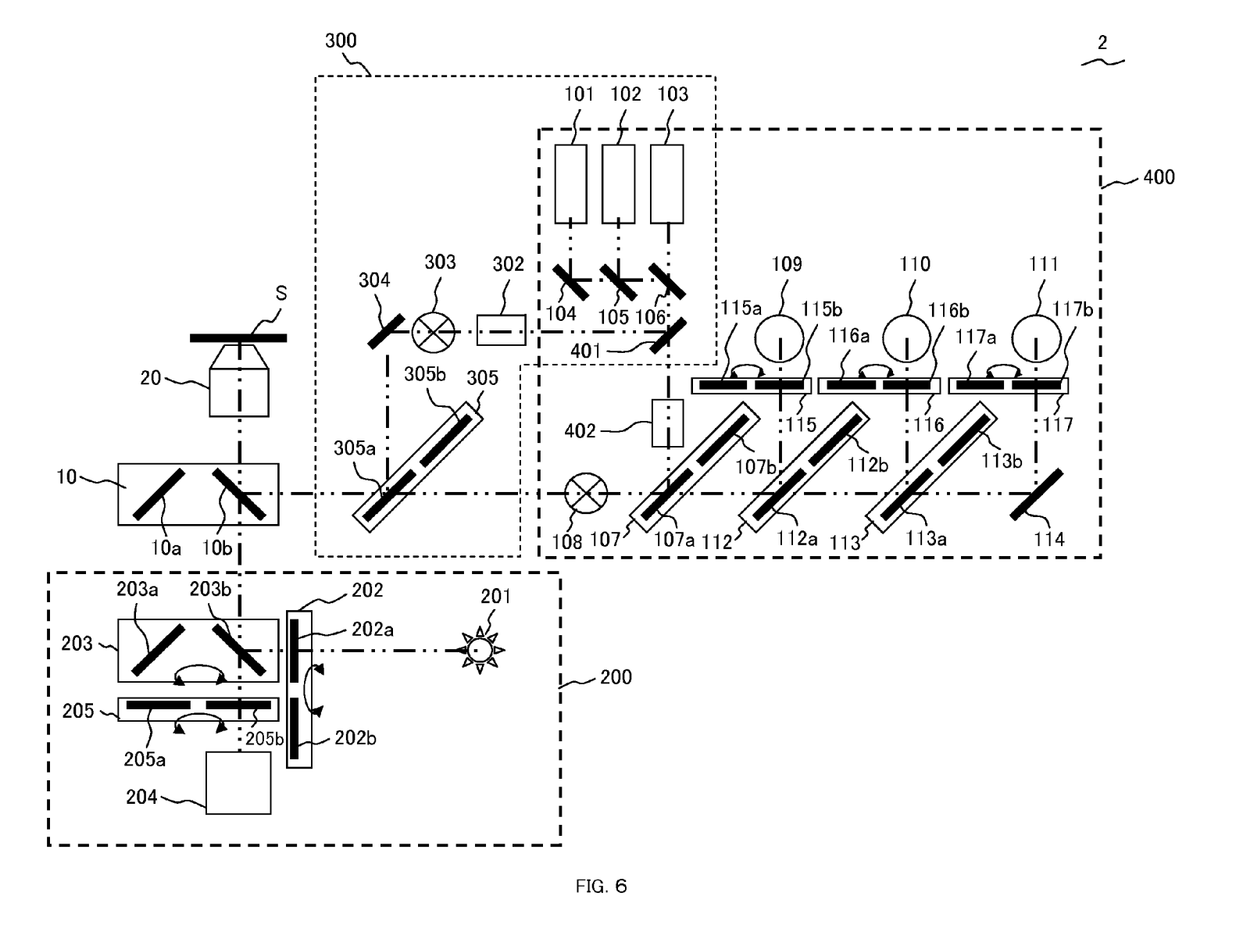
FIG. 6 illustrates an example of the configuration of a fluorescence observation apparatus according to Embodiment 2 of the present invention.

FIG. 6 illustrates an example of the configuration of a fluorescence observation apparatus according to the present embodiment. Firstly, the configuration of a fluorescence observation apparatus according to the present embodiment will be explained with reference to FIG. 6. In the actual apparatuses, a tube lens and a relay optical system that relays pupil, and the like is arranged as necessary at an earlier stage of a two-dimensional detector in a similar manner to FIG. 1. However, a relay optical system or the like is omitted in FIG. 6 so as to schematically illustrate a fluorescence observation apparatus.

A fluorescence observation apparatus 2 illustrated in FIG. 6 as an example is provided with: a laser scanning fluorescence observation unit 400 that observes a sample S by using a scanning unit to scan the sample S with laser light; the wide field fluorescence observation unit 200 that observes the sample S by planar-illuminating the sample S and by using a two-dimensional detector to detect fluorescence; and a stimulation unit 300 that shares two or more lasers with the laser scanning fluorescence observation unit 100 and optically stimulates a sample by using laser light from the two or more lasers, where laser scanning fluorescence observation and wide field fluorescence observation may be performed at the same time.

The fluorescence observation apparatus 2 is similar to the fluorescence observation apparatus 1 according to Embodiment 1, except that a stimulation unit 300 is included and a laser scanning fluorescence observation unit 400 is included instead of the laser scanning fluorescence observation unit 100. For this reason, the same reference signs are assigned to the same elements and the explanation is omitted, and differences from the fluorescence observation apparatus 1 will be mainly described.

The laser scanning fluorescence observation unit 400 is different from the laser scanning fluorescence observation unit 100 in that a half mirror 401 that divides the laser light from a laser shared with the stimulation unit 300 into a laser light for fluorescence observation and a laser light for optical stimulation is included, and that an acousto-optic tunable filter (hereinafter, referred to as AOTF) 402 that selects a laser light of any wavelength from the incident laser light is included. The laser scanning fluorescence observation unit 400 is similar to the laser scanning fluorescence observation unit 100 in the other aspects. The AOTF 402 is used to block the laser light emitted for optical stimulation.

The stimulation unit 300 shares with the laser scanning fluorescence observation unit 400 two or more lasers (i.e., the laser 101, the laser 102, and the laser 103), a unit that guides laser light from the two or more lasers onto the same optical path (e.g., the mirror 104, the dichroic mirror 105, and the dichroic mirror 106), and the half mirror 401.

The stimulation unit 300 further includes: an AOTF 302 that selects a laser light of any wavelength from the incident laser light; a galvanometer mirror 303 that stimulates a desired position on a sample by using laser light (stimulation light); a mirror 304; and a unit that combines the optical path from the stimulation unit 300 with the optical path from the laser scanning fluorescence observation unit 400 (e.g., a filter switching unit 305, a dichroic mirror 305a, and a dichroic mirror 305b). The AOTF 302 is used to block the laser light emitted for fluorescence observation.

Also in the fluorescence observation apparatus 2 as configured above, it is possible to determine the optical property of a barrier filter and an excitation filter according to the procedure depicted in FIG. 3, and to switch between barrier filters and to switch between excitation filters according to the procedure depicted in FIG. 5. Accordingly, similar advantageous effects to the fluorescence observation apparatus 1 according to Embodiment 1 may be achieved.

What is claimed is:

1. A fluorescence observation apparatus comprising:
a laser scanning fluorescence observation unit including a plurality of lasers, a scanning unit that scans a sample by laser light from the plurality of lasers, and a detector that detects fluorescence from the sample excited by the laser light;
a wide field fluorescence observation unit including a light source to planar-illuminate the sample, a plurality of excitation filters that are selectively arranged on an optical path of light from the light source and that respectively correspond to the plurality of lasers, and a two-dimensional detector that detects a fluorescence from the sample, wherein the sample is excited by light that has passed through an excitation filter arranged on the optical path of light from the light source; and
a dichroic mirror that combines an optical path of the laser light with the optical path of light from the light source;
wherein:
each of the plurality of excitation filters has an optical property in which a center wavelength of a transmissive band is approximately the same as an oscillation wavelength of a corresponding laser and a bandwidth of a transmissive band is approximately the same as a tolerance width of an oscillation wavelength of a corresponding laser;
the laser scanning fluorescence observation unit further includes a plurality of first barrier filters selectively arranged between the dichroic mirror and the detector, each of the first barrier filters corresponding to a respective one of the plurality of lasers;
the wide field fluorescence observation unit further includes a plurality of second barrier filters selectively arranged between the dichroic mirror and the two-dimensional detector, each of the second barrier filters corresponding to a respective one of the plurality of lasers;
the first barrier filter and the second barrier filter which correspond to a same laser have a same optical property; and
when fluorescence observation is performed by using both the laser scanning fluorescence observation unit and the wide field fluorescence observation unit, (i) an excitation filter from the plurality of excitation filters, which corresponds to another laser selected from the plurality of lasers, excluding a laser to be used for fluorescence observation, is arranged on the optical path of light from the light source, (ii) a first barrier filter from the plurality of first barrier filters, which corresponds to the laser to be used for fluorescence observation, is arranged between the dichroic mirror and the detector, and (iii) a second barrier filter from the plurality of second barrier filters, which corresponds to the another laser, is arranged between the dichroic mirror and the two-dimensional detector.

2. The fluorescence observation apparatus according to claim 1, wherein the light source is a light source with a continuous or discrete light source wavelength including oscillation wavelengths of the plurality of lasers.

3. The fluorescence observation apparatus according to claim 2, wherein the light source is a mercury lamp.

4. The fluorescence observation apparatus according to claim 2, wherein the light source is a white LED light source provided with a plurality of LED chips.

5. The fluorescence observation apparatus according to claim 2, wherein the light source is a white LED light source having a fluorescent material around an LED chip.

6. A fluorescence observation apparatus comprising:
a laser scanning fluorescence observation unit including a plurality of lasers, a scanning unit that scans a sample by laser light from the plurality of lasers, and a detector that detects fluorescence from the sample excited by the laser light;
a wide field fluorescence observation unit including a light source to planar-illuminate the sample, a plurality of excitation filters that are selectively arranged on an optical path of light from the light source and that respectively correspond to the plurality of lasers, and a two-dimensional detector that detects a fluorescence from the sample, wherein the sample is excited by light that has passed through an excitation filter arranged on the optical path of light from the light source;
a dichroic mirror that combines an optical path of the laser light with the optical path of light from the light source; and
a stimulation unit that shares the plurality of lasers with the laser scanning fluorescence observation unit and optically stimulates the sample by using laser light from the plurality of lasers;
wherein:
each of the plurality of excitation filters has an optical property in which a center wavelength of a transmissive band is approximately the same as an oscillation wavelength of a corresponding laser and a bandwidth of a transmissive band is approximately the same as a tolerance width of an oscillation wavelength of a corresponding laser;
the laser scanning fluorescence observation unit further includes a plurality of first barrier filters selectively arranged between the dichroic mirror and the detector, each of the first barrier filters corresponding to a respective one of the plurality of lasers;
the wide field fluorescence observation unit further includes a plurality of second barrier filters selectively arranged between the dichroic mirror and the two-dimensional detector, each of the second barrier filters corresponding to a respective one of the plurality of lasers; and
the first barrier filter and the second barrier filter which correspond to a same laser have a same optical property.

7. The fluorescence observation apparatus according to claim 6, wherein the light source is a light source with a continuous or discrete light source wavelength including oscillation wavelengths of the plurality of lasers.

8. The fluorescence observation apparatus according to claim 7, wherein the light source is a mercury lamp.

9. The fluorescence observation apparatus according to claim 7, wherein the light source is a white LED light source provided with a plurality of LED chips.

10. The fluorescence observation apparatus according to claim 7, wherein the light source is a white LED light source having a fluorescent material around an LED chip.

\* \* \* \* \*